(12) United States Patent
Buijink et al.

(10) Patent No.: US 7,763,564 B2
(45) Date of Patent: Jul. 27, 2010

(54) TITANIUM CATALYST, ITS PREPARATION AND ITS USE IN EPOXIDATION REACTIONS

(75) Inventors: Jan Karel Frederik Buijink, Amsterdam (NL); Johannes Jacobus Maria Van Vlaanderen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 134 days.

(21) Appl. No.: 11/743,003

(22) Filed: May 1, 2007

(65) Prior Publication Data

US 2007/0260074 A1 Nov. 8, 2007

(30) Foreign Application Priority Data

May 2, 2006 (EP) .................................. 06113369

(51) Int. Cl.
*B01J 27/135* (2006.01)
*B01J 27/045* (2006.01)
*B01J 27/06* (2006.01)
*B01J 21/00* (2006.01)
*C01B 33/12* (2006.01)
*C07D 303/00* (2006.01)

(52) U.S. Cl. ........................ 502/223; 502/224; 502/227; 502/229; 502/242; 502/350; 423/335; 423/336; 423/337; 423/338; 423/339; 549/12

(58) Field of Classification Search ................. 502/224, 502/227, 223, 239, 242, 350; 423/335–339; 549/512

See application file for complete search history.

(56) References Cited

U.S. PATENT DOCUMENTS

| 3,829,392 | A | | 8/1974 | Wulff | 252/430 |
|---|---|---|---|---|---|
| 3,923,843 | A | | 12/1975 | Wulff | 260/348.5 |
| 4,021,454 | A | * | 5/1977 | Wulff et al. | 549/529 |
| 4,228,261 | A | * | 10/1980 | Scholten et al. | 502/330 |
| 6,011,162 | A | | 1/2000 | Han et al. | 549/529 |
| 6,114,552 | A | | 9/2000 | Han et al. | 549/529 |
| 6,383,966 | B1 | * | 5/2002 | Han et al. | 502/63 |
| 7,125,819 | B2 | * | 10/2006 | Van Der Linden et al. | 502/102 |
| 7,294,727 | B2 | * | 11/2007 | Buijink et al. | 549/529 |
| 2005/0014960 | A1 | * | 1/2005 | Buijink et al. | 549/533 |

FOREIGN PATENT DOCUMENTS

| EP | 345856 | 12/1989 |
|---|---|---|
| EP | 525503 | 2/1993 |
| EP | 734764 | 10/1996 |
| GB | 1148689 | 4/1969 |
| WO | WO 9850374 A2 * | 11/1998 |
| WO | WO0248126 | 6/2002 |
| WO | WO2004050233 | 6/2004 |
| WO | WO2004050241 | 6/2004 |

\* cited by examiner

*Primary Examiner*—Patricia L Hailey

(57) ABSTRACT

The invention relates to a process for the preparation of a titanium catalyst which process comprises:
(a) drying a silica carrier at a temperature of from 300 to 800° C. to obtain a dried carrier;
(b) contacting the dried carrier obtained in step (a) with a gas stream containing titanium halide at a temperature in the range from 125° C. lower to 125° C. higher than the drying temperature of step (a) and at a pressure higher than 0.8 bar to obtain an impregnated carrier;
(c) calcining the impregnated carrier obtained in step (b) to obtain the titanium catalyst.

15 Claims, No Drawings

TITANIUM CATALYST, ITS PREPARATION AND ITS USE IN EPOXIDATION REACTIONS

This application claims the benefit of European Patent Application No. 06113369.0, filed May 2, 2006, which is incorporated herein by reference.

FIELD OF THE INVENTION

The present invention relates to a process for the preparation of a titanium catalyst, the titanium catalyst as such and to a process for the preparation of alkylene oxide with the catalyst.

BACKGROUND OF THE INVENTION

Titanium catalysts are known to be useful in the preparation of alkylene oxide. Processes for the preparation of titanium catalysts are also well known.

U.S. Pat. No. 6,114,552 describes the use of a high surface area silica support in preparing epoxidation catalysts. The support used in the invention of U.S. Pat. No. 6,114,552 has a surface area greater than 1100 m$^2$/g. The epoxidation catalyst is made by impregnation of the support with either a solution of a titanium halide in a non-oxygenated hydrocarbon solvent or a gas stream of titanium tetrachloride, and then calcining it.

Catalyst 1B is the only catalyst made in accordance with the invention of U.S. Pat. No. 6,114,552 which is prepared by impregnation of a silica support with a gas stream of titanium tetrachloride. The surface area of the support used for Catalyst 1B is 1140 m$^2$/g. This silica support is first calcined at 550° C. for 14 hours. The calcined and dried support thus obtained is then charged into a tubular reactor which is inter alia equipped with a heating mantle and a 3-neck round-bottom flask. The catalyst inside the tubular reactor is then heated to 400° C. Once this temperature is reached, water is added into the 3-neck round-bottom flask and this flask is heated with a heating mantle to reflux in order to distill the water through the catalyst bed. A heat gun is used to heat the round-bottom flask to drive any residual water through the bed. That is to say, in order to ensure that all of the water added into the flask is brought into contact with the support inside the tubular reactor. Once all of the water has disappeared from the round-bottom flask, the catalyst bed inside the tubular reactor placed on said flask, is cooled to 300° C. Such water treatment may, at least partially, result in hydrolysis of the support. It is not disclosed in U.S. Pat. No. 6,114,552 at what rate the bed temperature is decreased. Neither is it indicated if, and, if so, for how long the catalyst bed is maintained at 300° C. Therefore, as soon as said temperature is achieved, the silica support which has not been dried after the water treatment step, is subjected to the titanation step. In this titanation step, titanium tetrachloride is transferred to the 3-neck round-bottom flask. This flask is heated to reflux in order to distill the titanium tetrachloride through the catalyst bed. After said titanation the catalyst bed is heated at 700° C. for 0.5 hour resulting in a calcined catalyst. The final catalyst has a loading of 4.9 wt % titanium.

Comparative Catalysts 3A and 3B of U.S. Pat. No. 6,114,552 are also catalysts prepared by impregnation of a silica support with a gas stream of titanium tetrachloride. The surface area of their support is only 300 m$^2$/g. This silica support is first dried at 450° C. for 2 hours. The dried support thus obtained is then placed into a tubular reactor which is inter alia equipped with a heating mantle and a 3-neck round-bottom flask. The catalyst inside the tubular reactor is then heated to 200° C. Once this temperature is reached, titanium tetrachloride is added into the 3-neck round-bottom flask and this flask is heated with a heating mantle to reflux in order to distill the titanium tetrachloride through the catalyst bed. After said titanation the catalyst bed is heated at 600° C. for 2 hours resulting in a calcined catalyst. The final catalyst has a loading of 2.6 wt % titanium.

GB-A-1,148,689 relates to a process for preparing an olefin polymerization catalyst which comprises reacting alumina, silica or alumina-silica with a titanium halide at a temperature of from 300 to 700° C., followed by hydrolyzing and calcining in a hydrogen-containing atmosphere. In Example 10 of GB-A-1,148,689 silica is used as the carrier. This carrier is first calcined at 500° C. for 2 hours. The calcined and dried carrier thus obtained is then reacted with a gas stream containing titanium tetrachloride at a temperature of 375° C. for 2 hours. After completion of the reaction, dry nitrogen only was introduced for an additional ten minutes to purge the remaining titanium tetrachloride from the reactor. It is not indicated in GB-A-1,148,689 which temperature is applied during said purging. However, if said temperature is the reaction temperature of 375° C., then the time period of only 10 minutes is still too short, especially in combination with such relatively low temperature, to effect calcination of the impregnated carrier after having first purged all of the remaining titanium tetrachloride from the reactor. In order to achieve calcination, in general, a calcination time of at least 30 minutes may be required, as in the above-mentioned first calcination step (2 hours) and the second calcination step discussed below (4 hours). After said purging the impregnated carrier is hydrolyzed, dried at a temperature of 120° C. for 2 hours, and finally calcined by heating it at a temperature of 800° C. for 4 hours while passing dry hydrogen from which oxygen had been removed, over it.

EP-A-0,525,503 discloses a method for preparing a heterogeneous catalyst comprised of a support material and at least one catalytically active species. In Example 1 of EP-A-0,525,503 silica is used as the support material. The support is first pretreated for 16 hours at 450° C. in air. The dried support thus obtained is then pretreated for 4 hours in nitrogen at a partial vacuum of 70 mbar. It is not indicated in EP-A-0,525,503 which temperature is applied during said pretreatment with nitrogen. However, since after said latter pretreatment the temperature is increased up to the reaction temperature which is either 175 or 450° C., the temperature applied during said latter pretreatment must be lower than 450° C. Once the reaction temperature is achieved, titanium tetrachloride vapour is introduced for 2 hours into the reaction space using nitrogen gas as the carrier. The titanation reaction is performed at said partial vacuum of 70 mbar, which is in conformity with a preferred embodiment of the invention of EP-A-0,525,503 as discussed at column 5, lines 30-38. According to this preferred embodiment, the reaction between the vapour of the catalyst reagent and the support material takes place at a pressure ranging from 0.1 to 100 mbar. According to EP-A-0,525,503, an advantage of that partial vacuum is that purity of the reaction space can be improved and the diffusion rate increased. Finally, the impregnated silica support obtained in Example 10 of EP-A-0,525,503 is flushed with nitrogen gas for 2 hours at the reaction temperature. The final catalyst has a loading of 3.3 wt % titanium where the reaction temperature is 175° C., and a loading of 2.6 wt % titanium where the reaction temperature is 450° C.

There is a continuous interest in improving the selectivity of titanium catalysts to alkylene oxide. There is furthermore interest in improving the process for the preparation of such catalysts. We found a simple and attractive way to achieve this.

SUMMARY OF THE INVENTION

Surprisingly it was found that the selectivity of a titanium catalyst can be improved by using a catalyst preparation process wherein a specific combination of drying in terms of the drying temperature, impregnation in terms of the impregnation temperature and pressure, and calcination is used. The present invention now relates to a process for the preparation of a titanium catalyst which process comprises:

(a) drying a silica carrier at a temperature of from 300 to 800° C. to obtain a dried carrier;

(b) contacting the dried carrier obtained in step (a) with a gas stream containing titanium halide at a temperature in the range from 125° C. lower to 125° C. higher than the drying temperature of step (a) and at a pressure higher than 0.8 bar to obtain an impregnated carrier;

(c) calcining the impregnated carrier obtained in step (b) to obtain the titanium catalyst.

DETAILED DESCRIPTION OF THE INVENTION

Within the present specification, the expression "dried carrier obtained in step (a)" used in the description of step (b) of the process of the present invention means that between steps (a) and (b) no further treatment of the carrier, such as water treatment or hydrolysis, takes place.

Further, within the present specification, the expression "impregnated carrier obtained in step (b)" used in the description of step (c) of the process of the present invention means that between steps (b) and (c) no further treatment of the carrier, such as water treatment or hydrolysis, takes place.

By a titanium catalyst in this specification is understood a carrier that has been dried, impregnated with a titanium compound and calcined. The catalyst of the present invention is obtained by drying of a silica carrier followed by gas phase impregnation with a titanium halide, and finally calcination.

The combination of drying the silica carrier at a temperature of from 300 to 800° C., then gas phase impregnation of the dried carrier thus obtained at a temperature in the range from 125° C. lower to 125° C. higher than the drying temperature of step (a) and at a pressure higher than 0.8 bar, and finally calcination of the impregnated carrier thus obtained, results in catalysts having a lower titanium loading with an improved selectivity.

The temperature in impregnation step (b) is in the range from 125° C. lower than the drying temperature, preferably 100° C. lower than the drying temperature, more preferably 50° C. lower than the drying temperature, even more preferably 25° C. lower than the drying temperature to 125° C. higher than the drying temperature, preferably 100° C. higher than the drying temperature, more preferably 50° C. higher than the drying temperature, even more preferably 25° C. higher than the drying temperature. Most preferred is that the titanation temperature is within 10° C. below or above the drying temperature of step (a).

The pressure in impregnation step (b) is higher than 0.8 bar, that is to say higher than 800 mbar. Said pressure is preferably at least 0.9 bar, more preferably at least 0.95 bar and even more preferably at least 0.99 bar. Further, said pressure is preferably at most 5 bar, more preferably at most 3 bar and even more preferably at most 2 bar. Most preferred is that the pressure in impregnation step (b) is substantially equal to atmospheric pressure, that is to say around 1 bar. Where in this specification the term "bar" is used, "bar absolute" or "bara" is meant.

In principle, any silica carrier is suitable for use in the preparation process according to the present invention. Preferably, a silica gel carrier is used as silica carrier. Besides silica gels also synthetic silica carriers, like MCM-41, or precipitated silica powders can be used. Optionally, the carriers can be shaped in any desired form, by any method known to the skilled person.

It is known that contaminants can influence the performance of the final catalyst. For example sodium present in the silica carrier forms NaCl with chloride that negatively influences the performance of the catalyst. It has been found that gas phase impregnation according to the present invention gives especially good results if the silica carrier contains at most 1500 ppm of sodium, more specifically at most 1200 ppm of sodium, even more specifically at most 1000 ppm of sodium. Further, the silica carrier preferably comprises at most 500 ppm of aluminium, at most 500 ppm of calcium, at most 200 ppm of potassium, at most 100 ppm of magnesium and at most 100 ppm of iron.

If a silica gel carrier is used in a preferred embodiment of the present invention in principle any carrier derived from a silicon containing gel can be used. In general, silica gels are a solid, amorphous form of hydrous silicon dioxide. They usually contain three-dimensional networks of aggregated silica particles of colloidal dimensions. They are, for example, prepared by acidifying an aqueous sodium silicate solution to a pH of less than 11 by combining it with a strong mineral acid. The acidification causes the formation of monosilicilic acid $(Si(OH)_4)$, which polymerizes into particles with internal siloxane linkages and external silanol groups. At a certain pH the polymer particles aggregate, thereby forming chains and ultimately gel networks. Silicate concentration, temperature, pH and the addition of coagulants affect gelling time and final gel characteristics such as density, strength, hardness, surface area and pore volume. The resulting hydrogel is typically washed free of electrolytes, dried and activated. A suitable silica gel carrier would be silica support V432 (surface area of 320 $m^2/g$) and DAVICAT SI-1101 (surface area of 345 $m^2/g$), which are commercially available from Grace Davison.

Although silica carriers with a surface area of up to 1600 $m^2$/gram can be used, the silica gel carrier for use in the present invention preferably has a surface area of at most 1000 $m^2$/gram, more preferably at most 800 $m^2$/gram, even more preferably at most 650 $m^2$/gram, most preferably at most 400 $m^2$/gram. Generally, the surface area will be at least 10 $m^2$/gram, more specifically at least 20 $m^2$/gram. Silica gel carriers which were found especially suitable had a surface area of 345 $m^2/g$.

Preferably, silica gel carriers for use in the present invention have a weight average particle size of at most 2 millimeters. Particle sizes which were found to be especially suitable for use in the present invention were weight average particle sizes of from 0.2 to 1.8 mm, more specifically of from 0.4 to 1.6 mm, most specifically of from 0.6 to 1.6 mm.

Drying according to the present invention comprises subjecting the silica carrier to a temperature of from 300 to 800° C. The temperature of the drying of step (a) is considered to be the temperature of the silica carrier. Drying can be carried out in the absence or in the presence of an inert gas such as nitrogen. Preferably, the drying is carried out at a temperature higher than 400° C., more preferably at a temperature higher than 550° C. The temperature chosen depends on the practical circumstances. Not all reactors can be used for subjecting the carrier to a relatively high temperature of about 800° C. However, such high temperature has been found to give especially good results.

The kind of silica carrier used and the pretreatment of the silica carrier influence the time during which the drying is to be carried out. The drying will generally be carried out during from 15 minutes up to 10 hours, more specifically of from 1 to 8 hours, more specifically of from 1 to 5 hours.

It has been found especially advantageous if the drying and gas phase impregnation is carried out subsequently in one reactor, without cooling to room temperature or transfer to an other reactor in between the two steps.

It has been found especially advantageous if the amount of titanium halide supplied in step (b) is such that the catalyst obtained is loaded with 0.1 up to 2.5 wt % titanium, preferably 0.5 up to 2.3 wt % titanium, based on the total weight of the catalyst.

It has been found that the relatively low loadings of 0.1 up to 2.5 wt % give a catalyst with a higher selectivity to the desired alkylene oxide than similar catalysts with loadings higher than 2.5 wt %. Preferably, titanium or a titanium compound, such as a salt or an oxide, is the only metal and/or metal compound present. Applicants now found that the loading of 0.1 up to 2.5 wt % Ti on the silica carrier gives a bonding of the titanium compounds and the silica which is especially advantageous for the selectivity. Furthermore, with these loadings, relatively less titanium is leached from the catalyst when used over a longer period in the epoxidation reactor. During the production of the catalyst itself less titanium has to be used leading to a reduction of fouling of the reactor where the production of the catalyst takes place.

Generally, the silica carrier is contacted with the titanium halide in the course of from 0.1 and 10 hours, more specifically of from 0.5 to 6 hours. With halide is meant fluoride, chloride, iodide or bromide. The time of impregnation is taken to be the time during which the silica carrier is in contact with gaseous titanium halide. Preferably, the silica carrier is contacted with a similar amount of titanium halide during the full time of the impregnation. However, it will be clear to someone skilled in the art that deviations from this are allowable such as at the start of the impregnation, at the end of the impregnation and for relatively short time intervals during impregnation. Titanium halides which can be used comprise tri- and tetra-substituted titanium complexes which have of from 1 to 4 halide substituents with the remainder of the substituents, if any, being alkoxide or amino groups. The titanium halide can be either a single titanium halide compound or can be a mixture of titanium halide compounds. Preferably, the titanium halide comprises at least 50 wt % of titanium tetrachloride, more specifically at least 70 wt % of titanium tetrachloride. Most preferably, the titanium halide is titanium tetrachloride.

The present invention comprises the use of a gas stream comprising titanium halide. Preferably, the gas stream consists of titanium halide optionally in combination with an inert gas. If an inert gas is present, the inert gas preferably is nitrogen. Especially selective catalysts were found to be obtainable with the help of a gas stream solely consisting of titanium halide. In such process, the preparation is carried out in the absence of a carrier gas. However, limited amounts of further gaseous compounds are allowed to be present during the contact between the silicon containing carrier and the gaseous titanium halide. The gas in contact with the carrier during impregnation preferably consists for at least 70 wt % of titanium halide, more specifically at least 80 wt %, more specifically at least 90 wt %, most specifically at least 95 wt %. Specific preferred processes have been described in European application EP-A-1567261.

Gaseous titanium halide can be prepared in any way known to someone skilled in the art. A simple and easy way comprises heating a vessel containing titanium halide to such temperature that gaseous titanium halide is obtained. If inert gas is to be present, the inert gas can be led over the heated titanium halide.

The reaction product of step (b), the impregnated carrier, still contains too much chlorine in relation to titanium. If one would use the impregnated carrier as a catalyst, the product stream would contain chlorine, and an extra step would be needed to remove this chlorine. Furthermore, the selectivity to alkylene oxide of the impregnated carrier makes it less suitable for use as a catalyst.

Calcining the reaction product of step (b) removes hydrogen chloride. In EP-A-0345856 the calcination is explained in more detail. Preferably, the calcination is carried out at a temperature of at least 300° C., more preferably at a temperature of at least 400° C., even more preferably at a temperature of at least 550° C. Preferably, calcination in step (c) of the present process is carried out at a temperature which is higher than the temperature in impregnation step (b). From a practical point of view, the calcination temperature applied is at most 800° C. Preferably, the calcination is carried out at a temperature of at most 650° C. At temperatures above 650° C. the calcination equipment becomes more expensive, since special construction materials must be used for building the reactors that can withstand these high temperatures. Most preferred is that the calcination is performed at approximately the same temperature as the temperature of the initial drying step. Calcination, in the present invention, results in the titanium catalyst. Normally, a calcination time in the range of 30 minutes up to 24 hours is applied.

Generally, the catalyst will be subsequently hydrolysed and optionally silylated before being used in the reaction. Therefore, the present invention further relates to a process that further comprises (d) hydrolysing the catalyst as obtained in step (c) to obtain a hydrolysed catalyst; (e) optionally contacting the hydrolysed catalyst obtained in step (d) or the catalyst obtained in step (c) with a silylating agent to obtain a silylated catalyst. Hydrolysis of the catalyst may remove Ti-halide bonds. The hydrolysis of the catalyst is suitably carried out with steam at a temperature preferably in the range of from 150 to 400° C., more preferably in the range of from 250 to 350° C.

Silylation of the (hydrolysed) catalyst can be carried out by contacting the (hydrolysed) catalyst with a silylating agent, preferably at a temperature of between 100 and 425° C., more preferably at a temperature of between 150 to 350° C. Suitable silylating agents include organosilanes like tetra-substituted silanes with $C_1$-$C_3$ hydrocarbyl substituents. A very suitable silylating agent is hexamethyldisilazane. Examples of suitable silylating methods and silylating agents are, for instance, described in U.S. Pat. No. 3,829,392 and U.S. Pat. No. 3,923,843 which are referred to in U.S. Pat. No. 6,011,162, and in EP-A-734764.

As mentioned above, it is well known in the art to produce alkylene oxides, such as ethylene oxide and propylene oxide, by epoxidation of the corresponding olefin using a hydroperoxide such as hydrogen peroxide or an organic hydroperoxide as the source of oxygen. The hydroperoxide can be hydrogen peroxide or any organic hydroperoxide such as tert-butyl hydroperoxide, cumene hydroperoxide and ethylbenzene hydroperoxide. The alkene will generally be ethylene or propene which gives as alkylene oxide, ethylene oxide or propylene oxide. The catalyst prepared according to the present invention has been found to give especially good results in such process. Therefore, the present invention further relates to a process for the preparation of alkylene oxide which process comprises contacting a hydroperoxide and alkene with a heterogeneous epoxidation catalyst and withdrawing a product stream comprising alkylene oxide and an alcohol and/or water, in which process the catalyst is according to the present invention.

A specific organic hydroperoxide is ethylbenzene hydroperoxide, in which case the alcohol obtained is 1-phenyl ethanol. The 1-phenylethanol usually is converted further by dehydration to obtain styrene.

Another method for producing propylene oxide is the coproduction of propylene oxide and methyl tert-butyl ether (MTBE) starting from isobutane and propene. This process is well known in the art and involves similar reaction steps as the styrene/propylene oxide production process described in the previous paragraph. In the epoxidation step tert-butyl hydroperoxide is reacted with propene forming propylene oxide and tert-butanol. Tert-butanol is subsequently etherified into MTBE.

A further method comprises the manufacture of propylene oxide with the help of cumene. In this process, cumene is reacted with oxygen or air to form cumene hydroperoxide. Cumene hydroperoxide thus obtained is reacted with propene in the presence of an epoxidation catalyst to yield propylene oxide and 2-phenyl propanol. The latter can be converted into cumene with the help of a heterogeneous catalyst and hydrogen. Specific suitable processes are described for example in WO 02/48126.

The conditions for the epoxidation reaction according to the present invention are those conventionally applied. For propene epoxidation reactions with the help of ethylbenzene hydroperoxide, typical reaction conditions include temperatures of 50 to 140° C., suitably 75 to 125° C., and pressures up to 80 bar with the reaction medium being in the liquid phase.

The invention is further illustrated by the following Examples.

EXAMPLES

The silica gel carrier used in the examples was a wide pore silica gel (Grace Davison DAVICAT SI 1101) having a surface area of 345 m$^2$/g and a pore volume of 1 ml/g. Substantially all particles had a particle size between 0.6 and 1.6 mm. Silica intake was 75 g in a quartz fixed bed reactor.

Example A (Comparative)

Comparative catalyst A was prepared by drying the silica carrier at a temperature of 265° C. for 2 hours in a reactor, followed by cooling the carrier to a temperature of 208° C. where titanation took place by dosing 14 g of titanium tetrachloride in the gas phase (75 vol % in nitrogen) over a period of 70 minutes. Subsequently the catalyst was calcined at 600° C. for 7 hours under a nitrogen flow of 55 Nl/hr. Heating and cooling rates were 100° C./hr below 300° C. and 50° C./hr above 300° C.

Example B (Comparative)

Comparative catalyst B was prepared by drying the silica carrier at a temperature of 450° C. for 2 hours in air (heating rate 300° C./hr), followed by cooling the carrier to a temperature of 300° C. where titanation took place by dosing 14 g of titanium tetrachloride in the gas phase (75 vol % in nitrogen) over a period of 70 minutes. Subsequently the catalyst was calcined at 690° C. for 7 hours under a nitrogen flow of 55 Nl/hr. Heating and cooling rates were 100° C./hr below 300° C. and 50° C./hr above 300° C.

Example 1 (According to the Invention)

Catalyst 1 was prepared by drying the silica carrier at 600° C. for 2 hours and cooling it down to 575° C. in a nitrogen flow of 55 Nl/hr. Subsequently the silica carrier was titanated with titanium tetrachloride at a temperature of 575° C. by dosing 11 g of titanium tetrachloride in the gas phase (75 vol % in nitrogen) over a period of 70 minutes. The impregnated carrier was heated to 600° C. and calcined for 7 hours under a nitrogen flow of 55 Nl/hr. Heating and cooling rates were 100° C./hr below 300° C. and 50° C./hr above 300° C.

Example 2 (According to the Invention)

Catalyst 2 was prepared by drying the silica carrier at 450° C. for 2 hours and cooling it down to 425° C. in a nitrogen flow of 72 Nl/hr. Subsequently the silica carrier was titanated with titanium tetrachloride at a temperature of 425° C. by dosing 12 g of titanium tetrachloride in the gas phase (75 vol % in nitrogen) over a period of 70 minutes. The impregnated carrier was heated to 600° C. and calcined for 7 hours under a nitrogen flow of 55 Nl/hr. Heating and cooling rates were 100° C./hr below 300° C. and 50° C./hr above 300° C.

Example 3 (According to the Invention)

Catalyst 3 was prepared by drying the silica carrier at 450° C. for 2 hours and cooling it down to 425° C. in a nitrogen flow of 72 Nl/hr. Subsequently the silica carrier was titanated with titanium tetrachloride at a temperature of 425° C. by dosing 13 g of titanium tetrachloride in the gas phase (75 vol % in nitrogen) over a period of 70 minutes. The impregnated carrier was heated to 450° C. and calcined for 7 hours under a nitrogen flow of 55 Nl/hr. Heating and cooling rates were 100° C./hr below 300° C. and 50° C./hr above 300° C.

Subsequent Treatment

All calcined catalysts were subsequently contacted with steam at 325° C. during 4 hours. The steam flow consisted of resp. 3.5 g/hr for the first 2 hours and 5 g/hr for the subsequent 2 hours with 8 Nl of nitrogen per hour as carrier gas. Finally, all the catalysts were silylated at 185° C. during 2 hours by passing hexamethyldisilazane through the catalyst bed in gas phase at a rate of 18 g per hour in a nitrogen flow of 1.4 Nl per hour.

The catalyst as prepared in example 1 (Catalyst 1) was also tested without carrying out a steaming and silylation step. This catalyst was noted as Cat 1*.

Catalytic Performance

The catalytic performance of the titanium catalyst samples was tested in an 1-octene batch test, where 25 ml of a mixture containing 7.5 wt % ethylbenzene hydroperoxide (EBHP) and 36 wt % 1-octene in ethyl benzene (EB) was allowed to react with 0.5 g of titanium catalyst at 40° C. while mixed thoroughly. After 1 hour the mixture was cooled in ice water to end the reaction and the concentrations of EBHP and 1-octylene oxide were determined by Near Infrared (NIR) analyses. Near Infrared (NIR) analyses were carried out by near-infrared spectroscopy using a Bomen WORKIR 160 analyser.

In table 1, the conversions and the selectivities are given. The conversion is the percentage of ethylbenzenehydroperoxide which has been converted. The selectivity is the molar ratio of 1-octylene oxide formed to EBHP converted.

TABLE 1

| Cat | Drying/ Titanation/ calcination T (° C.) | Ti on catalyst (wt %) | Conv. EBHP after 1 hr (%) | Conv. EBHP after 1 hr/ wt % Ti | Sel. to 1-octyl. ox. at 50-60% conv. EBHP (%) |
|---|---|---|---|---|---|
| A | 265/208/600 | 3.78 | 54.5 | 14.4 | 93.7 |
| B | 450/300/690 | 2.6 | 57.7 | 22.2 | 93.5 |
| 1 | 600/575/600 | 1.65 | 40.2 | 24.4 | 94.9 |
| 2 | 450/425/600 | 2.16 | 48.9 | 22.6 | 94.3 |
| 3 | 450/425/450 | 2.24 | 23.7 | 10.6 | 94.8 |
| 1* | 600/575/600 | 1.65 | 46.1 | 27.9 | 84.7 |

It has been found for each of the above catalysts that over the whole of at least the range for conversion of EBHP of 50-60%, the selectivity to 1-octylene oxide remained the same. It can be concluded from the results as presented in table 1 that catalyst 1, 2 and 3 have improved selectivity over both catalysts A and B. In comparison with catalyst B the use of high calcination temperature is prevented leading to savings in time and savings on expensive construction materials for these high temperatures.

The invention claimed is:

1. A process for the preparation of a titanium catalyst which process comprises:
   (a) drying a silica carrier at a temperature of from 100 to 800° C. to obtain a dried carrier;
   (b) contacting the dried carrier obtained in step (a) with a gas stream containing titanium halide at a temperature in the range from 125° C. lower to 125° C. higher than the drying temperature of step (a) and at a pressure higher than 0.8 bar to obtain an impregnated carrier;
   (c) calcining the impregnated carrier obtained in step (b) to obtain the titanium catalyst
   wherein the silica carrier in step (a) has a surface area of at most 800 m²/gram.

2. A process according to claim 1, wherein the process further comprises
   (d) hydrolysing the catalyst as obtained in step (c) to obtain a hydrolysed catalyst.

3. A process according to claim 2 wherein the process further comprises
   e) contacting the hydrolysed catalyst obtained in step d) with a silylating agent to obtain a silylated catalyst.

4. A process according to claim 1, wherein the process further comprises
   (e) contacting the catalyst obtained in step (c) with a silylating agent to obtain a silylated catalyst.

5. A process according to claim 1, wherein step (b) is performed at a temperature in the range from 50° C. lower to 50° C. higher than the drying temperature of step (a).

6. A process according to claim 1, wherein step (c) is performed at a temperature in the range of from 300 to 800° C.

7. A process according to claim 1, wherein the amount of titanium halide supplied in step (b) is such that the catalyst obtained is loaded with 0.1 up to 2.5 wt % titanium, based on the total weight of the catalyst.

8. A process according to claim 1, wherein the gas stream of step (b) consists of titanium halide.

9. A process according to claim 1, wherein the silica carrier has a surface area of at most 650 m²/g.

10. A process for the preparation of alkylene oxide which process comprises contacting a hydroperoxide and an alkene with the catalyst prepared according to claim 7 and withdrawing a product stream comprising an alkylene oxide and an alcohol and/or water.

11. A process according to claim 10, wherein the alkene is propene and the alkylene oxide is propylene oxide.

12. A process according to claim 10, wherein the hydroperoxide is ethylbenzene hydroperoxide and the alcohol is 1-phenyl ethanol.

13. A process according to claim 12, wherein the process further comprises dehydration of 1-phenylethanol to obtain styrene.

14. A process for the preparation of a titanium catalyst which process comprises:
   (a) drying a silica carrier at a temperature of from 450 to 800° C. to obtain a dried carrier;
   (b) contacting the dried carrier obtained in step (a) with a gas stream containing titanium halide at a temperature in the range from 125° C. lower to 125° C. higher than the drying temperature of step (a) and at a pressure higher than 0.8 bar to obtain an impregnated carrier;
   (c) calcining the impregnated carrier obtained in step (b) to obtain the titanium catalyst
   wherein the silica carrier in step (a) has a surface area of at most 800 m²/gram.

15. A process according to claim 14, wherein step (a) is carried out at a temperature of from 550 to 800° C.

* * * * *